United States Patent [19]

Torgeson

[11] 4,177,816
[45] Dec. 11, 1979

[54] HEAT EXCHANGER FOR BLOOD

[75] Inventor: William L. Torgeson, Edina, Minn.

[73] Assignee: Sci-Med Life Systems, Inc., Minneapolis, Minn.

[21] Appl. No.: 890,077

[22] Filed: Mar. 27, 1978

[51] Int. Cl.² ............................................... A61F 7/00
[52] U.S. Cl. ...................................... 128/400; 165/172
[58] Field of Search .............. 128/399, 400, 401, 402; 165/172, 177, 46, 158; 23/258.5

[56] References Cited

U.S. PATENT DOCUMENTS

| 3,140,716 | 7/1964 | Harrison | 128/399 |
| 3,238,944 | 3/1966 | Hirschhorn | 128/400 |
| 3,315,681 | 4/1967 | Poppendiek | 128/399 |
| 3,768,977 | 10/1973 | Braufield et al. | 128/400 |
| 3,807,958 | 4/1974 | Brumfield et al. | 23/258.5 |
| 4,047,563 | 9/1977 | Kurata | 165/158 |
| 4,111,659 | 9/1978 | Bowley | 422/48 |
| 4,132,587 | 1/1979 | Lankenau et al. | 159/27 A |

*Primary Examiner*—Lawrence W. Trapp
*Attorney, Agent, or Firm*—James R. Haller

[57] ABSTRACT

A disposable, tube-and-shell heat exchanger for controlling the temperature of blood. The tube portion includes a plurality of parallel tubes having serpentine inserts therein in heat-exchange contact with smooth inner walls of the tubes. The tubes are of sufficient number, length and flow area to permit gentle laminar blood flow at 37° C. of up to five liters per minute.

12 Claims, 9 Drawing Figures

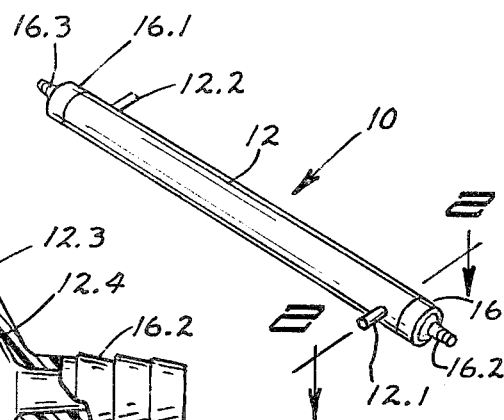
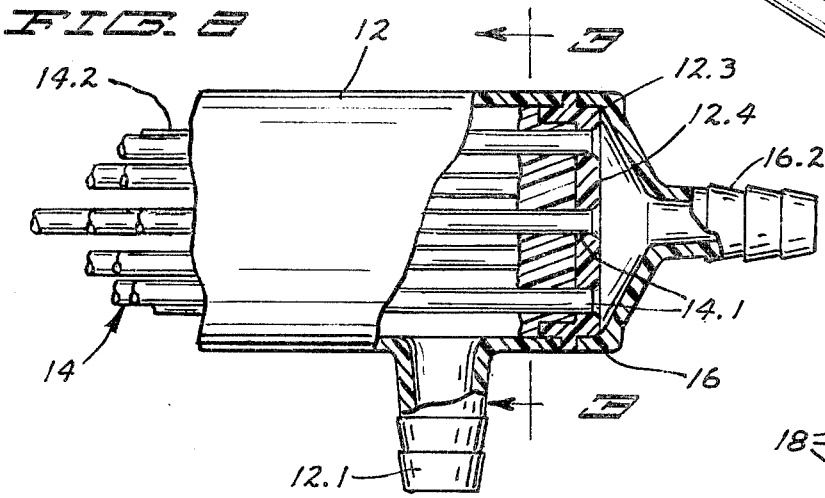
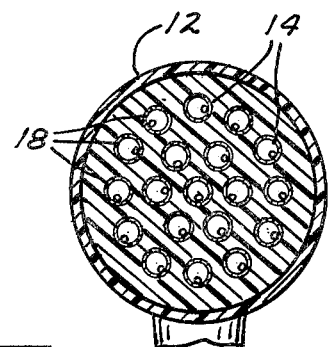
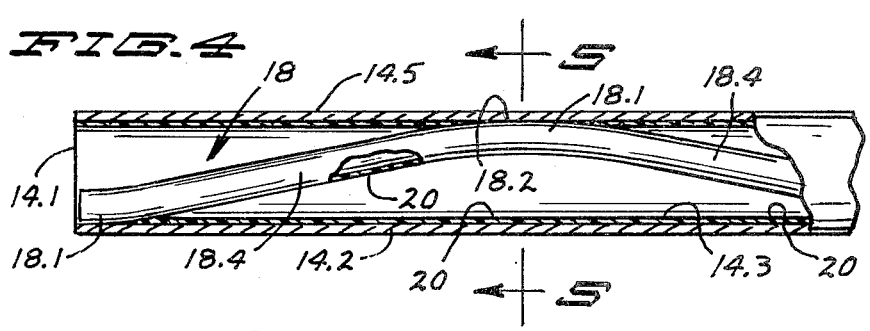
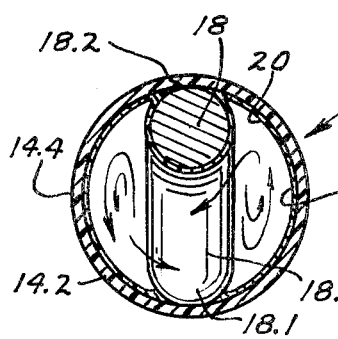
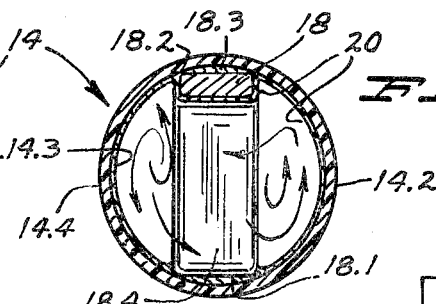
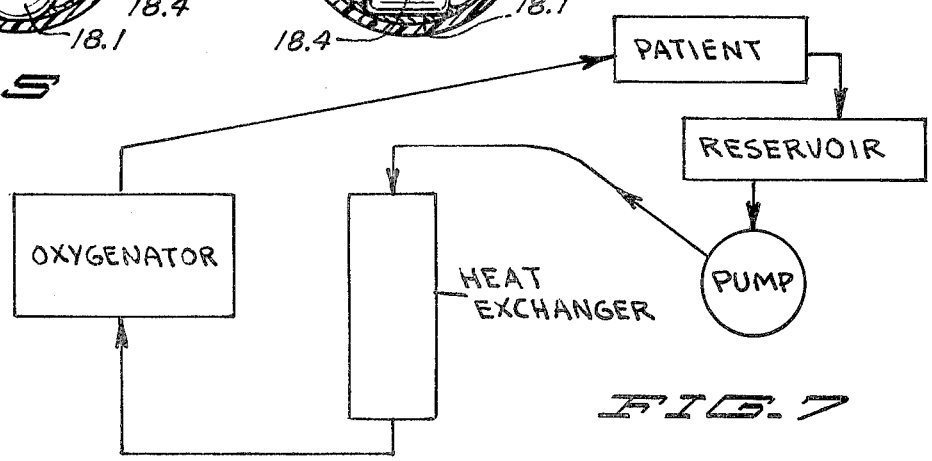

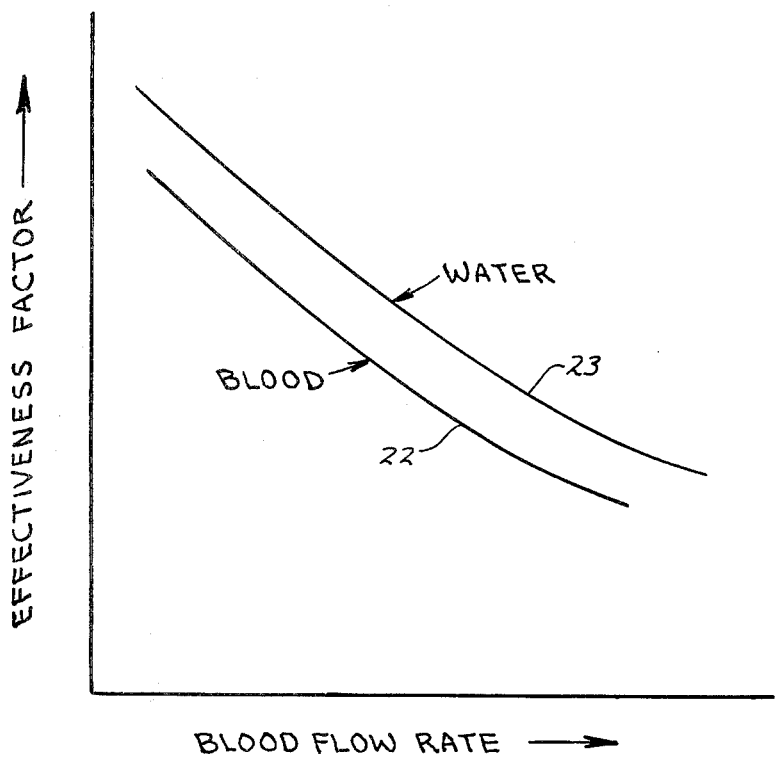
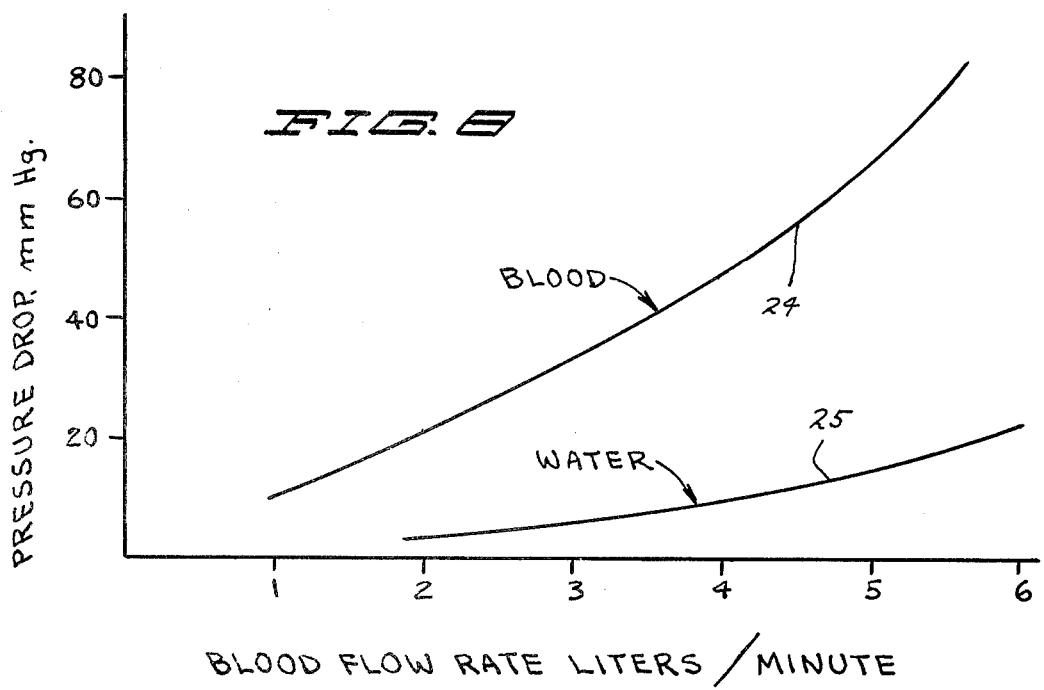

HEAT EXCHANGER FOR BLOOD

BACKGROUND OF THE INVENTION

Heat exchangers for blood are used extensively in sophisticated medical processes. When cardiovascular surgery is performed, for example, a "heart-lung" machine is employed to pump and oxygenate a patient's blood while the patient's heart is stopped. Often, the patient's body temperature is artifically lowered to reduce the patient's physiological processes to thereby reduce the patient's need for oxygenated blood. During coronary revascularization, profound hypothermia in conjunction with topical cooling protects the myocardium during ischemic periods at the time of surgery. A typical heart-lung machine may include, in series, a reservoir to collect blood from the patient, a pump to maintain blood flow, a heat exchanger to warm or cool the blood and an oxygenator, blood returning to the patient from the oxygenator. Other elements, of course, may be included within the extra corporeal circuit such as means for removing bubbles from the blood and the like.

It will be understood that a considerable volume of blood or other fluid is required to "prime" or to fill a heart-lung machine so that the same may be operated. In practice, the machine may be primed with non-cellular fluids with or without the addition of blood from a blood bank or previously taken from the patient.

The heat exchanger in the apparatus described above may be employed to reduce the blood temperature of a patient before heart surgery begins, and subsequently may be used to reheat the blood to a normal body temperature at the conclusion of the operation. Reusable tube-and-shell heat exchangers of stainless steel are widely used for this purpose. The conditions which are imposed upon such reusable heat exchangers, however, render heat exchangers of this type extremely expensive and costly. The cleaning effort after each use is arduous. With one commerical heat exchanger of this type, for example, the heat exchanger must be completely disassembled after each use, thoroughly cleaned, and then reassembled—a task which requires a number of hours. The reassembled heat exchanger must, of course, be sterilized, and great care and skill is required in the cleaning operation.

Generally, a heat exchanger of the type described must be capable of rapid heat exchange over rather narrow temperature differentials, and yet must avoid turbulence or other disturbances with blood which might lead to blood damage. Thus, large pressure drops and turbuence in the flow of blood through the heat exchanger—which ordinarily would be desired to increase the rate of heat transfer—must be avoided. Further, the heat exchanger should require the smallest possible amount of blood or other liquid for "priming".

It would be highly desirable to provide an inexpensive, easily manufactured, disposable blood heat exchanger which would provide good heat exchange over narrow temperature differentials, which would operate with a low pressure differential thereacross, and which would maintain the blood in gentle laminar flow through the exchanger.

BRIEF SUMMARY OF THE INVENTION

The instant invention relates to a disposable, efficient tube-and-shell heat exchanger for blood which is charactrized by having a low priming volume and which is operational with a low pressure drop with blood in laminar flow therethrough.

The heat exchanger of the invention includes a plurality or "bundle" of generally parallel tubes having smooth inner walls, and a jacket about the tubes having inlet and outlet means for a heat exchanger medium. The heat exchanger includes inlet and outlet manifold means of low volume for supplying blood to and for collecting blood from the tubes. The tubes are characterized by having elongated inserts therein, each insert having periodic reverse bends throughout its length providing the insert with a serpentine configuration with portions of the insert between successive periodic bends desirably lying in generally the same plane. Outer surfaces of the bends are in heat exchange contact with the smooth inner walls of the tubes. The inserts serve to reduce the priming volume of the tubes, but yet permit the blood to flow through the tubes in laminar flow under low pressure differentials. The inserts increase the rate of heat transfer.

The tubes are sufficient in number, length, and flow area to provide a blood flow rate from up to about five liters per minute at a temperature of 37° C., and desirably at a pressure drop across the tubes of not more than about 85 mm. of mercury. Desirably, the inserts reduce the area of the tubes available for blood flow by about 5 to about 25 percent, and perferably, about 8 to about 15 percent. The priming volume of the tubes, taken as a whole, does not exceed about 125 ml. of blood. Yet, notwithstanding the presence of the inserts and the corresponding reduced priming volume, blood flows through the heat exchanger in gentle laminar flow, and the blood flow is characterized by a Reynolds number of not greater than about 400 and desirably in a range of about 100 to about 400.

BRIEF DESCRIPTION OF THE DRAWING

FIG. 1 is a perspective view of a heat exchanger of the invention;

FIG. 2 is a broken-away view in partial cross-section taken along line 2—2 of FIG. 1;

FIG. 3 is a cross-sectional view taken along line 3—3 of FIG. 2;

FIG. 4 is a broken-away view in partial cross-section showing a single tube employed in the heat exchanger of FIG. 1;

FIG. 5 is a cross-sectional view taken along line 5—5 of FIG. 4;

FIG. 6 is a cross-sectional view depicting a modified embodiment of the tube and insert of FIG. 5;

FIG. 7 is a schematic representation of a blood circulating system employing the heat exchanger of the invention;

FIG. 8 is a graphical representation of the pressure drop characteristics of a heat exchanger of the invention at varying blood flow rates; and FIG. 9 is a graph showing trends in the variance of the "effectiveness factor" with blood flow rate.

DETAILED DESCRIPTION

With reference to FIG. 1, the heat exchanger of the invention is designated generally as 10. The exchanger includes an outer, generally tubular shell 12 having inlet and outlet ports 12.1, 12.2 adjacent its ends. The ports 12.1, 12.2 may be on the same side or on different sides of the shell 12. Generally discshaped end caps 12.3 (FIG. 2) completely close the ends of the shell. A bundle of thin-walled tubes 14 are arranged in a spaced, parallel relationship with the ends 14.1 of the tubes extending into orifices formed in the end caps. The ends of the tubes are sealed to the disc by layers of potting compound 12.5. Generally cup-shaped manifolds 16, 16.1 are received at the ends of the shell and provide low-volume compartments communicating with the tube ends. Conduits, labeled 16.2, 16.3, respectively communicate with and protrude from the manifolds 16, 16.1. In use, it will be understood that a heat exchange medium such as water is flowed into the shell port 12.1 and thence is conveyed within the shell in heatexchange contact with the tubes, the medium finally passing outwardly through the port 12.2. Blood enters the manifold 16.1 through conduit 16.3 and passes thence into the tubes 14 in a direction counter to the direction of the heat exchange medium. Blood exits from the tubes into the manifold 16 and passes from the heat exchanger through the conduit 16.2.

The tubes 14 desirably are made of a heat-conductive metal such as a aluminum, and are provided with thin walls 14.2 and a smooth interior 14.3. Within each tube is positioned an elongated insert 18 (FIGS. 3-6) having a series of reverse bends 18.1 therein providing the insert with a generally serpentine configuration. The inserts are also desirably of metal, and preferably are of generally circular or rectangular cross-section as shown best in FIGS. 5 and 6, respectively. The outer surfaces of the inserts at the points of bending are in metal-to-metal contact (indicated as 18.2) with the smooth interior metallic walls of the tubes, thereby providing good heat transfer between the inserts and the tube walls. It will be understood that the inserts 18 may be triangular or oval in cross-section, or may be of any cross-section offering low resistance to blood flow and desirably having no sharp edges or grooves.

The outer surfaces 14.4 of the tubes may be smooth or finned or fluted, or may be provided with any other desired surface configuration. Baffles may be placed in the path of the heat exchange medium, if desired. It has been found that the limiting resistance to heat transfer is between the blood and the tubes 14 rather than between the tubes and the heat exchange medium.

A thin, biologically-acceptable (having no significant adverse influence on blood) continuous coating designated generally as 20 is applied to the interiors of the tubes and to the exposed surfaces of the inserts after the inserts have been inserted in the tubes. As shown in FIGS. 5 and 6, the coating extends as a thin, unbroken film from the the interior walls 14.3 of the tubes to the adjacent surfaces of the inserts. In addition, the coating is continued to and beyond the tube ends to coat the manifolds 16, 16.1, conduits 16.2, 16.3 and exposed end disc surface 12.4. Blood passing into or out of the manifolds is shielded from contact with the blood-confronting metal surfaces of the tubes or inserts and the plastic surfaces of the manifolds, discs and conduits. Blood compatible coatings are known to the art, and include polyurethane (e.g., a mixture of "Vorite 689" and "Polycin 942", products of N. L. Ind., Inc.) and silicone rubber.

With reference to FIG. 5, it will be noted that the circular insert, at each bend, contacts the tube inner wall at but a single point. The circular insert desirably has a diameter in cross-section of not more than about 40 percent of the tube inner diameter. The ribbon-like insert of FIG. 4, having a generally rectangular cross-section with rounded edges, contacts the interior surface of the tubes at each bend at two points. The small, normally open area (designated 18.3 in FIG. 4) between the contact points is generally open but may be filled with the coating material 20. The maximum cross-sectional dimension of such ribbon-like inserts desirably is not greater than about 90 percent of the inner tube diameter.

The inserts are configured so as to have between about two and about eight reverse bends therein in a length of tubing cross-section dimension of a circular insert may typically be on the order of one-third the inner diameter of the tube, and the sections 18.4 of the inserts between the reverse bends are generally straight and desirably in the same plane, although some twisting of the inserts may be permitted, e.g., one 180° twist in a length of tubing equal to 500 times the inner tube diameter. The coating 20 on the exposed metal surfaces of the tubes and inserts is exceedingly thin, and may be on the order of 0.001 inches in thickness. The coating thickness is sufficiently great to effectively shield the metal surfaces of the tubes and inserts from blood contact. The presence of the coating has only a very small influence on the rate of heat transfer.

In the embodiment shown in FIGS. 1-4, the inner diameter of the shell may be on the order of 1.5 inches, and the lengths of the tubes may be on the order of 15¾ inches. The tubes themselves may be of aluminum and may have an outer diameter of about 0.2 inches and an inner diameter of about 0.18 inches. The embodiment shown in FIGS. 1-3 employs nineteen such tubes in parallel, the tubes being supported by the discs 12.3 and each tube being spaced by a given distance from its neighboring tubes.

Blood flowing through the tubes is caused by the inserts to describe a gentle swirling pattern as generally shown by the arrows in FIGS. 5 and 6. The blood, at a flow rate of up to about five and preferably six liters per minute, nonetheless passes through the tubes in gentle laminar flow, and the flow is characterized by a Reynolds number of not greater than about 400 and desirably in the range of from about 100 to about 400, based upon the effective hydraulic diameter of the tubes and the means blood velocity. As will be more fully discussed below, the gentle swirling action provided by the inserts causes gentle mixing of the flowing blood and increase the diffusion of heat, thus contributing to rapid heat transfer. The rate of heat transfer is augmented by heat conduction in the inserts and between the inserts and the tube walls.

The total volume ("priming volume") of the tubes of the heat exchanger, should not be greater than about 150 ml, and desirably is not greater than about 125 ml. Desirably, the inserts reduce the area available within the tubes for blood flow by not more than about 25 percent and desirably from about 8 to about 15 percent. The dimensions provided above with reference to the heat exchanger of FIGS. 1-3 are, of course, exemplary only. It is necessary only that the number, length and flow area of the tubes with inserts be sufficient to provide a laminar blood flow rate through the tubes of up to about five liters per minute and desirably up to six liters per minute at a temperature of 37° C. The pressure drop across the tubes preferably is not more than about 85 mm. of mercury. The inner diameters of the tubes may vary up to a half inch or more with the length or number of the tubes being decreased accordingly.

Notwithstanding the relatively small priming volume and laminar flow characteristics of the heat exchanger of the invention, the heat exchange characteristics of the exchanger are comparable with those of the most expensive and sophisticated blood heat exchangers now available.

FIG. 9 depicts generally the dependence on flow rate of the "effectiveness factor". "Effectiveness factor" is defined as:

$$\frac{\text{(temperature of blood out)} - \text{(temperature of blood in)}}{\text{(temperature of water in)} - \text{(temperature of blood in)}}$$

The curves 22, 23 of FIG. 9 provide rough comparisons of blood and of water, respectively, as the liquid flowing through the tubes 14. It will be noted that blood is the more difficult liquid to heat or cool. This difference in "effectiveness factor" is characteristic of heat exchangers in general, and reflects the fact that blood is a more complex liquid than water and that blood and water have different thermal and kinematic properties.

With reference to the heat exchanger dimensioned as indicated above, FIG. 8 compares flow rate with pressure drop. The curves 24, 25 of FIG. 8 refer to blood and to water, respectively, as the liquid flowing through the tubes 14, and are illustrative of differences in the flow properties of blood and water. The experiments from which curves 24, 25 were derived employed the above-described heat exchanger with water as the heat exchange medium flowing at a rate of 15–20 liters per minute. The difference between the temperatures of the incoming water heat exchange medium and the liquid (blood or water) entering the manifold 16.3 was 10° C.

The inserts 18 are of critical importance in attaining good heat transfer. For example, the effectiveness factor for the above-described heat exchanger with inserts was twice that of the exchanger without inserts.

Blood flowing through the heat exchanger described above incurred negligible damage, as measured by plasma hemoglobin analysis and blood platelet counts before and after passing through the exchanger. The lack of blood damage is believed due to the laminar flow characteristics afforded blood within the tubes, and also by employment of the continuous coating within the tubes which not only provides a blood-compatible surface but which further smooths any interior tube or insert surface defects.

FIG. 7 presents schematically the general route taken by blood of a patient through one heart-lung machine during openheart surgery. Blood ordinarily is taken from a large vein of the patient, and drains by gravity at a rate of e.g., 1–5 liters per minute or thereabouts to a small reservoir positioned below the level of the patient. The reservoir serves to insure that the remainder of the blood flow circuitry remains full at all times. A flow rate of 1–5 liters per minute approximates the pumping capacity of the human heart during periods of low physical stress. The blood from the reservoir is pumped through the heat exchanger, as shown. A heat exchange medium, such as water, is fed at a constant rate to the heat exchange shell as described above. The temperature differential between the entering blood and the entering heat exchange medium desirably is not greater than about 10° C. and the temperature of the heat exchange medium desirably does not exceed 42° C. Blood which has been warmed or cooled to the desired temperature passes from the heat exchanger to an oxygenator, and then is returned to the patient via a large artery. When low blood flow rates are desired, the heat exchanger may be placed immediately upstream of the reservoir and may function largely by gravity flow. The heat exchanger in this case desirably employs inserts of the type shown in FIG. 6, which appear to offer less resistance to flow than the inserts of FIG. 5.

It is desirable that the heat exchanger be positioned upstream from the oxygenator in the event that the blood is to be heated. The capacity of blood to absorb oxygen decreases with increasing blood temperature. To avoid bubble formation, it is apparent that the blood should not be further heated after passing through the oxygenator.

The shell 12, and caps 12.3 and manifolds may be made of a plastic, preferably transparent, such as polycarbonate. The tubes 14 and inserts 18 are of metal, preferably aluminum. The manifolds may be solvent welded to the end caps, and the latter may be solvent welded to the ends of the shell. The inserts 18 desirably are fashioned separately. Assembly of the heat exchanger may involve first positioning the ends of the tubes in one of the end caps, sliding the shell over the assembly, and positioning the other end cap into the other ends of the tubes. The inserts are forced into the tubes, and are retained in the tubes by friction. The manifolds are then positioned as shown in FIG. 2, and the manifolds, end caps and shell are cemented or solvent welded to provide a rigid structure. A polymeric potting compound such as polyurethane is introduced, sequentially, through the conduits 12.1, 12.2 about the juncture of the tubes with the end caps to provide sealing layers of which one is shown as 12.5 in FIG. 2. The potting compound is cured at temperatures of up to 50° C. to avoid damage due to thermal stress when the heat exchanger is used. Finally, a thin solution of a biologically-acceptable polymer such as a polyurethane is drawn upwardly through one of the conduits to completely coat all blood-contacting surfaces of the heat exchanger, following which the coating is air-dried. The above-described assembly is done in clean-room conditions, and the resulting heat exchangers are checked for leaks and are subsequently sterilized and packaged. It will be evident that the manufacture and assembly of the heat exchanger and of its various parts are particularly suited to relatively inexpensive automated production techniques.

Thus, manifestly there has been provided a blood heat exchanger which is inexpensive and which hence can be thrown away after a single use. The heat exchanger of the invention, however, is nonetheless characterized by having a high effectiveness factor and a low priming volume, and by operating under a low pressure differential with minimal is any damage to blood.

While we have described a preferred embodiment of the present invention, it should be understood that various changes, adaptations, and modifications may be made therein without departing from the spirit of the invention and the scope of the appended claims.

What is claimed is:

1. A disposable heat exchanger for controlling the temperature of blood, comprising a plurality of generally parallel tubes having smooth inner walls, inlet and outlet means for supplying blood to and for collecting blood from the tubes, a jacket about the tubes having inlet and outlet means enabling the flow of a heat exchange medium through the jacket and in heat exchange proximity with the tubes, the tubes being characterized by including elongated inserts therein, each insert having periodic reverse bends providing the insert with a serpentine configuration, outer surfaces of the bends being in heat-exchange contact with inner walls of the tubes, the tubes with inserts being of sufficient number, length and flow area to enable gentle, laminar blood flow through the tubes at 37° C. at a rate of up to about 5 liters per minute.

2. The heat exchanger of claim 1 wherein the inserts are ribbon-like in configuration and have a generally rectangular cross-section with rounded edges, the maximum cross-sectional width of the inserts being not greater than about 90 percent of the inner diameter of the tubes.

3. The heat exchanger of claim 1 wherein the inserts are generally circular in cross-section and have a diameter not greater than about 40 percent of the inner diameter of the tubes.

4. The heat exchanger of claim 1 including a thin, continuous, biologically-acceptable coating disposed upon all blood-confronting surfaces of the tubes and inserts.

5. The heat exchanger of claim 1 in which the total priming volume of the tubes with inserts is not greater than about 125 milliliters.

6. The heat exchanger of claim 5 so constructed and arranged as to provide a flow of blood, under a pressure drop of 85 mm of mercury and at a temperature of 37° C., at a rate of not less than about 5 liters per minute and wherein the latter blood flow is characterized by a Reynolds number of not greater than about 400.

7. The heat exchanger of claim 1 in which the number of reverse insert bends in a length of tubing equal to ten times the tubing inner diameter, is from about 2 to about 8.

8. The blood heat exchanger of claim 1 in which the tubes and inserts are of metal and are in metal-to-metal contact with one another, the interior of each tube and the insert therewithin having a continuous, thin, biologically-acceptable coating thereon.

9. A disposable heat exchanger for controlling the temperature of blood, the heat exchanger comprising a plurality of metal tubes having smooth interior walls and circular cross-sections, inlet and outlet means for supplying blood to and for collecting blood from the tubes, heat-exchange means for applying a heat exchange medium to exterior surfaces of the tubes, the tubes having elongated metal inserts therein, each insert having periodic reverse bends along its length providing the insert with a serpentine configuration, exterior surfaces of the inserts at such bends lying in metal-to-metal contact with interior surfaces of the tubes and being retained in the tubes by friction between the contacting surfaces of the tubes and inserts, the interiors of the tubes and surfaces of the associated inserts having a continuous, thin, biologically-acceptable coating thereon, the tubes with inserts being sufficient in number, length and flow area to provide, at a pressure drop across the tubes of not greater than about 85 mm of mercury and at a blood temperature of about 37° C. a laminar flow of blood characterized by a Reynolds number of not greater than about 400 and a blood flow rate of not less than about 5 liters per minute.

10. The heat exchanger of claim 9 in which the total priming volume of the tubes with inserts is not greater than about 125 milliliters.

11. The heat exchanger of claim 10 in which the heat exchange means comprises a jacket formed about the tubes and having inlet and outlet means permitting counter current flow of a heat exchange medium about the tubes, the heat exchanger having a heat exchange effectiveness factor at a blood flow rate of 2 liters per minute of not less than about 0.5, the effectiveness factor being defined as $$\frac{\text{(temperature of blood in)} - \text{(temperature of blood out)}}{\text{(temperature of blood in)} - \text{(temperature of heat exchange medium in)}}$$

12. The heat exchanger of claim 10 in which the inserts are of sufficient size as to reduce the area of the tubes available for blood flow by about 5 to about 25 percent.

* * * * *

UNITED STATES PATENT AND TRADEMARK OFFICE
CERTIFICATE OF CORRECTION

PATENT NO. : 4,177,816
DATED : December 11, 1979
INVENTOR(S) : William L. Torgeson It is certified that error appears in the above-identified patent and that said Letters Patent are hereby corrected as shown below:

Column 1, line 39: Change "in" to read "is"
Column 1, line 52: Change "turbuence" to read "turbulence"
Column 1, line 68: Change "ractrized" to read "racterized"
Column 2, line 6 : Change "exchanger" to read "exchange"
Column 3, line 21: Omit the word "a"
Column 4, line 10: After the word "tubing", add the following: "having a length to inner diameter ratio"
Column 6, line 51: Change "is" to "if"

Signed and Sealed this

Sixth Day of May 1980

[SEAL]

Attest:

SIDNEY A. DIAMOND

*Attesting Officer*  *Commissioner of Patents and Trademarks*